United States Patent [19]

Rapoport et al.

[11] Patent Number: 5,072,732
[45] Date of Patent: *Dec. 17, 1991

[54] NMR INSTRUMENT FOR TESTING FOR FLUID CONSTITUENTS

[75] Inventors: Uri Rapoport, Oak Park; Richard Panosh, Lisle, both of Ill.

[73] Assignee: Advanced Techtronics, Inc., Chicago, Ill.

[ * ] Notice: The portion of the term of this patent subsequent to Oct. 24, 2006 has been disclaimed.

[21] Appl. No.: 427,001

[22] Filed: Oct. 23, 1989

Related U.S. Application Data

[63] Continuation of Ser. No. 904,000, Sep. 4, 1986, Pat. No. 4,875,486.

[51] Int. Cl.$^5$ ............................................. A61B 5/055
[52] U.S. Cl. ................... 128/653.2; 324/308; 324/312; 324/321; 324/322
[58] Field of Search ...................... 128/653 A, 653 SC; 324/308, 312, 318, 322, 321, 309; 436/173

[56] References Cited

U.S. PATENT DOCUMENTS 4,875,486 10/1989 Rapoport et al. ............... 128/653 A

*Primary Examiner*—Ruth S. Smith
*Attorney, Agent, or Firm*—Jones, Day, Reavis & Pogue

[57] ABSTRACT

There is disclosed herein a nuclear magnetic resonance apparatus for testing body fluids for a constituent, for example, blood for glucose. The apparatus includes a principal magnet, a magnetizable coil, and a circuit for energizing the coil for energizing and realigning molecules and detecting changes resulting from relaxation of said field and analyzing said changes. The apparatus is compact and adapted to receive and test an extremity or vessel carrying a body fluid. The coil is constructed to be positioned adjacent the extremity or vessel to be tested. Circuit means are provided for energizing the coil to energize and realign molecules adjacent said coil, so as to permit molecules adjacent said coil to assume an aligned position and for sensing changes in position when the coil is deenergized, which is indicated by spectra having peaks corresponding to various molecular bonds. The circuit also includes means for comparing the actual value of a peak for a first constituent to a predetermined value for the peak of said first constituent and determining the actual value of a second constituent from a predetermined relationship between the values of the peaks for the first and second constituents. Specifically, predetermined water and glucose peaks are compared with the measured water and glucose peaks for determining the measured glucose concentration.

1 Claim, 8 Drawing Sheets

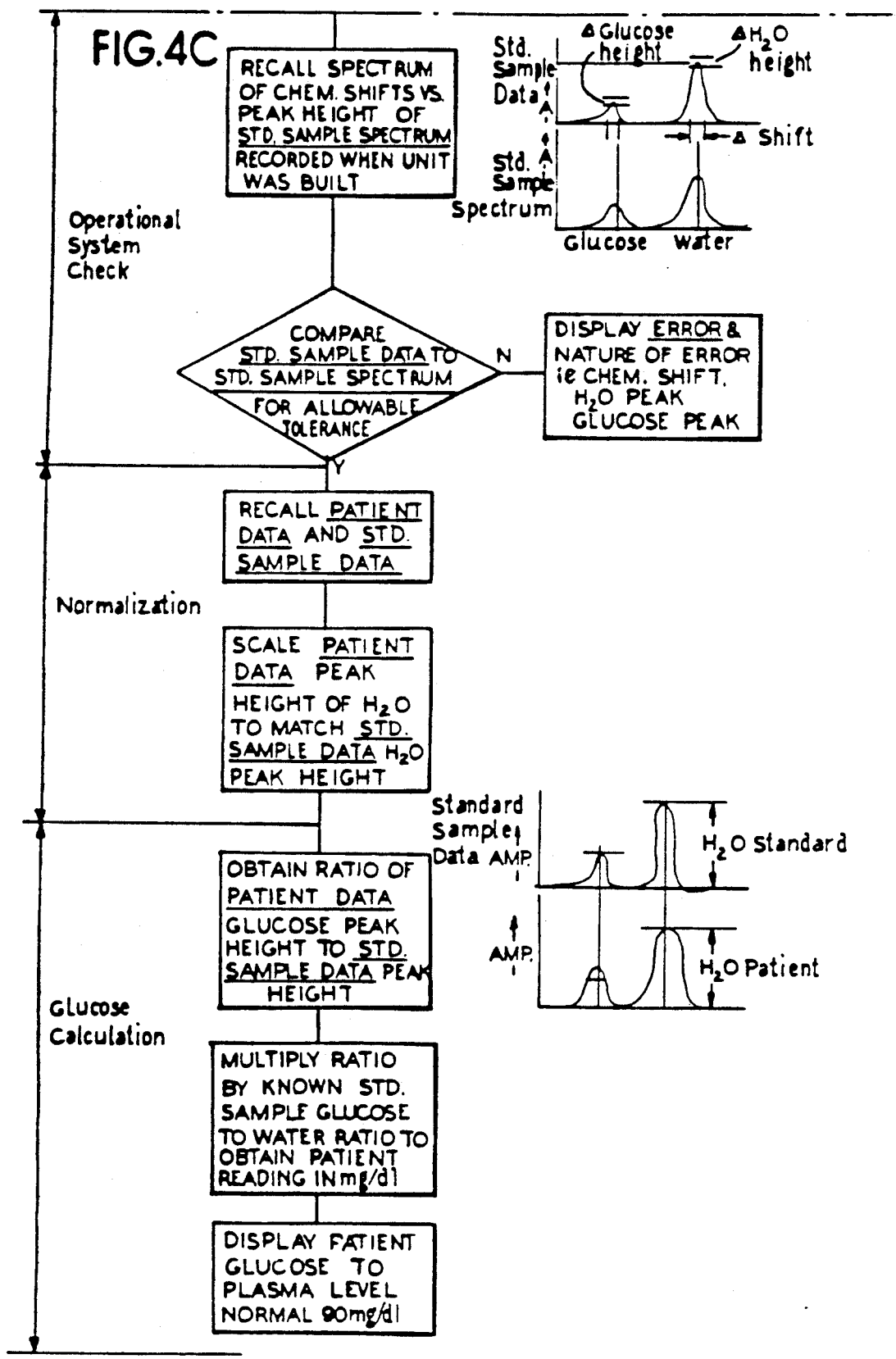

NMR INSTRUMENT FOR TESTING FOR FLUID CONSTITUENTS

This is a continuation of application Ser. No. 904,000, filed Sept. 4, 1986, now U.S. Pat. No. 4,875,486.

BACKGROUND OF THE INVENTION

This invention primarily relates to a method and to an instrument for use in medical diagnosis, and in particular, to detecting and determining glucose concentration in blood.

Diabetes is a health problem affecting many individuals and its prevalence is increasing. The usual treatment for diabetes is single or multiple insulin injections daily. Insulin is available in slowly or rapidly absorbed forms, which may be injected alone or in combination. Such insulin injections have been effective in treating the disease and in prolonging life.

Presently in order to determine if insulin is needed, blood is withdrawn from a patient and is tested for glucose concentration by a litmus-type indicator test. If indicated, insulin is taken by the patient.

This type of testing has several problems. For example, the testing is periodic, and thus the administration of insulin is periodic which can result in wide variations in glucose concentration over time and peaks in the glucose concentration. Such variations can have physiological effects which may be adverse to the patient.

It has been recognized that it is desirable to administer insulin periodically on demand and in response to changes in glucose levels. One such system is disclosed in Albisser A. "Devices for the Control of Diabetes Melletus". Proc. IEEE 67 No. 9, 1308-1310 (1979), wherein a servo system is employed which continuously withdraws blood from a patient and analyzes the same for glucose. Using a computer or microprocessor, calculations are made from the withdrawn sample as to the need for insulin, and in response thereto, insulin is administered. This system has only been used for short periods and has a disadvantage in that the system is invasive (i.e., the patient is catheterized continuously for withdrawing blood samples).

The litmus-type system has the disadvantage in that it is invasive and the patient is periodically and repeatedly pricked for blood samples.

It is therefore an object of this invention to provide a glucose testing device which can be used to monitor a patient's glucose level continuously, if desired, so as to provide a more uniform administration of insulin and a more uniform glucose concentration in the blood over time.

It is another object to provide a glucose monitoring system which is noninvasive and does not require periodic blood withdrawal to determine glucose levels.

It is sometimes desirable to test body fluids for other constituents. For example, law enforcement officers test individuals for alcohol content of their blood using a breathalyzer. However, breathalyzer tests may be inaccurate in that non-ingested alcohol, such as in mouthwashes, will provide false results.

It is another object of this invention to provide a noninvasiave diagnosis apparatus for use in determining the concentration of various constituents of body fluids such as glucose and alcohol and drugs.

Nuclear magnetic resonance (NMR) is a diagnostic technique which is used widely for medical imaging and medical diagnosis. In NMR, the test object is subjected to a first or biasing magnetic field to align previously randomly oriented $^1H$ protons in the nuclei and a second field or burst of energy to increase the energy of a selected nucleus. When the second magnetic field or energy source is turned of, the return to the first alignment releases energy which is detected and analyzed. This release is analyzed or processed to form an image or spectrum. From the spectrum, the presence of particular molecular bonds can be observed and associated with various molecules or materials from which the concentration of that molecule or material can be determined.

NMR machines are most frequently used for imaging sections of a human body and require large magnets, for example, superconducting magnets. The machines are therefore quite large and expensive. Furthermore, the NMR testing of fluids has required invasive sample withdrawal techniques, which sample was then tested in the larger machines.

Using such NMR machines, blood serum has been analyzed and a spectra of the $^1H$ resonance developed. In such spectra, identifiable peaks are obtained for water, glucose and ethanol. In reported tests, blood serum has been taken from animals, placed in a container and excited so as to yield the $^1H$ spectra, which is then analyzed. Unfortunately, NMR testings are not common nor conveniently available. The reason is believed to be that the equipment is generally large, complex and expensive, and is therefore available only at selected centers, such as hospitals, universities, and other similar research and test sites. The equipment therefore is not normally used for blood or body fluid analysis as more convenient and less expensive alternatives are available.

Another disadvantage in present NMR tests is that they are conducted on fluid samples which are withdrawn from the patient by the usual invasive techniques.

It is therefore an object of this invention to provide a more convenient NMR instrument for use in analyzing body fluid samples.

It is a further object of this invention to provide an NMR instrument for use in analyzing body fluid for glucose.

It is Yet another object to provide a portable NMR instrument for use by a person having diabetes to analyze his blood for glucose concentration.

It is yet a further object to provide an NMR instrument for use by a diabetic in noninvasively analyzing his blood serum for glucose concentration.

It is a still further object of the invention to provide an NMR method and apparatus to test for other substances, for example, alcohol and drugs.

These and other objects of this invention will become apparent from the following disclosure and appended claims.

SUMMARY OF THE INVENTION

This invention provides a method and a portable NMR instrument for use in noninvasively analyzing body fluids for the concentration of various constituents. Specifically, a diabetic can use the instrument to noninvasively and substantially instantaneously analyze his blood for glucose, thereby eliminating the need to invasively obtain a blood sample which is then tested. Using the device disclosed herein, a patient can periodically, frequently if necessary, a nd painlessly analyze his blood for glucose concentration. This device may also be useful in analyzing body fluids for alcohol or drugs.

In one form, the device is portable and provided with means for receiving an extremity of the patient, such as a finger, and exposing the extremity to a first or biasing magnetic field and a second field or energy source. Sensors are provided for sensing the rates of relaxation or energy release so as to develop the spectrum. Analytical means are coupled to the sensors for receiving and analyzing the signals emitted discriminating between various peaks, comparing the amplitude or height of various peaks, such as water and glucose, and normalizing the analysis by reference to a standard sample so as to obtain the concentration of constituents in the tested materials.

On of the principal components of the NMR instrument is the first or biasing magnet for providing the first magnetic field. In this device the biasing magnet is physically much smaller than the magnets used in standard NMR machines. For example, the magnet may be one pound in weight and may exhibit a field strength of at least five to six kilogauss. Another component is a coil apparatus for applying a second field or energy to the test sample and sensing the energy released therefrom. A single coil or multiple coils can be used. Yet another important element of this invention is the electronic circuit used for the analysis. This circuit is controlled by a microprocessor that is programmed to control the application of the second field or energy source and cooperates in detecting and analyzing the spectra received from the sample when the field is relaxed. Operation of the microprocessor is disclosed herein.

Other specific features of the instrument are disclosed hereinafter.

BRIEF DESCRIPTION OF THE DRAWINGS

FIGS. 4a to 4c are flow charts showing the operation of the instrument;

DESCRIPTION OF THE PREFERRED EMBODIMENT

Figure 1:
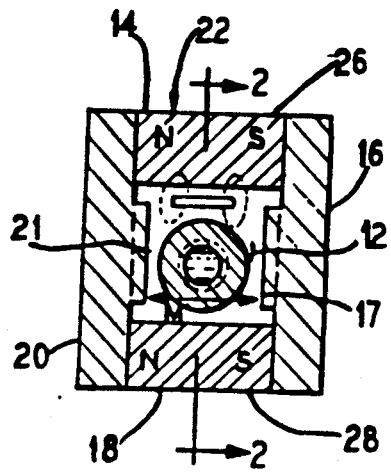
FIG. 1 is a vertical cross-sectional view of an instrument according to this invention.
Figure 2:
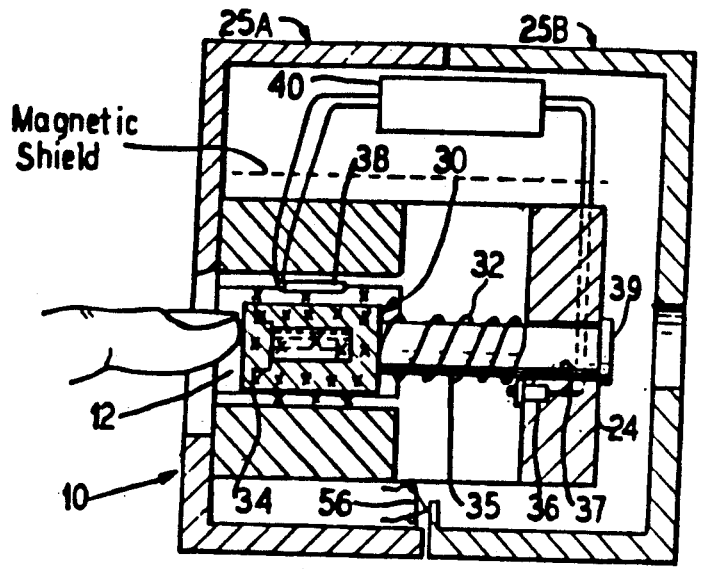
FIG. 2 is a vertical cross-sectional view taken along line 2—2 of FIG. 1 and also showing a housing and other components.
Figure 3:
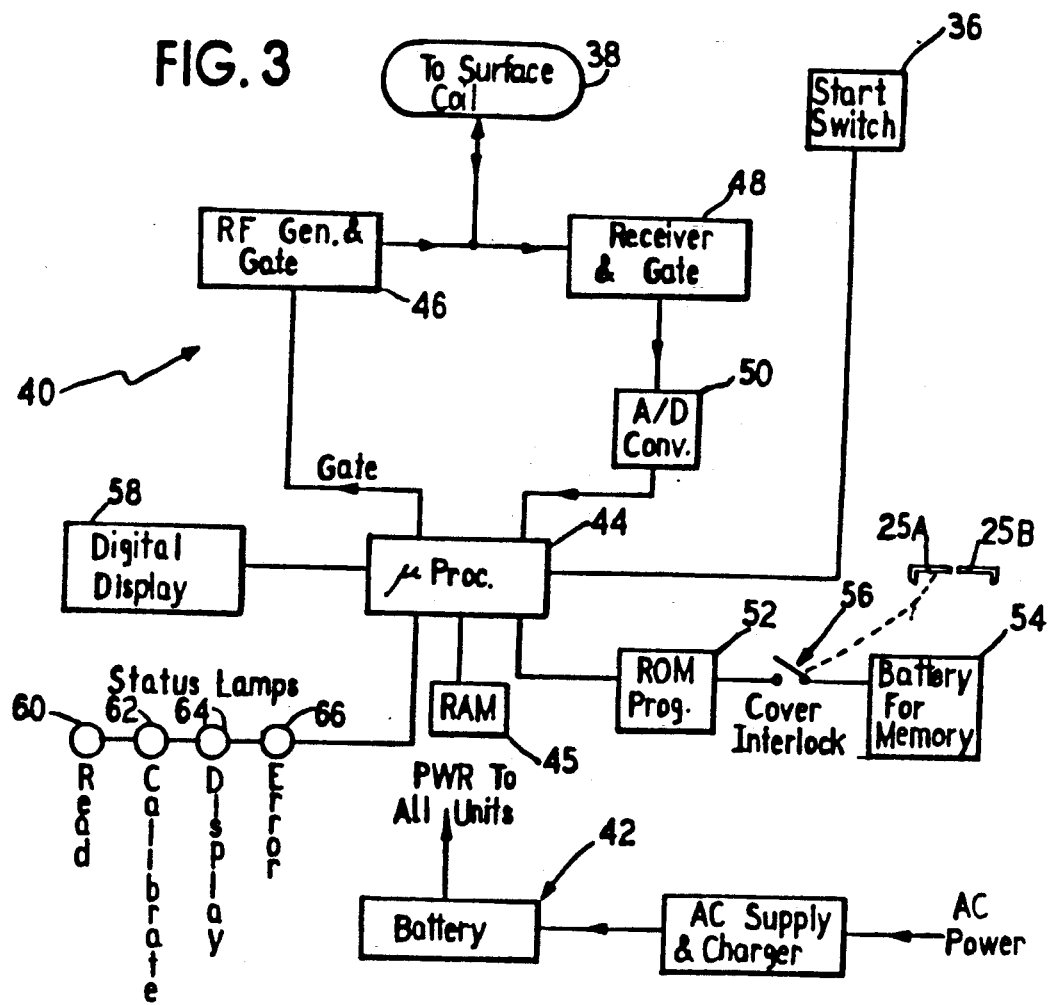
FIG. 3 is a block-type schematic diagram for the circuitry to operate the instrument.

Referring now to FIGS. 1-3, a first embodiment of the test instrument is shown. Other embodiments and features will be discussed after consideration of principal features of this invention by way of the first embodiment.

The test instrument 10 is shown as including a box-shaped assembly which defines a finger-receiving recess 12 therein. The assembly includes a body section 14 defined by the top, bottom and elongated side walls 16, 18, 20 and 22 and the back wall 24. The assembly is enclosed in a two piece cover or housing 25A and 25B within which the electronic components discussed hereinafter are also enclosed. Alternatively, the electronics can be enclosed in a separate housing connected to the body section. A pair of first or biasing permanent magnets 26 and 28 form the top and bottom walls 18 and 22, are positioned opposite one another and provide the first aligning magnetic field. It is to be noted that the poles of the respective magnets are aligned so that the field is additive and provide constructive interference, and the pole pieces or shoes shape the magnetic field in the finger-receiving recess 12. This alignment is shown by the "X" designation which indicates that the magnetic field from the magnets passes through the recess 12 in the same direction, in FIG. 2, into the paper.

A sample holder or container 34 for a standard sample starting apparatus 30 is shown positioned in the recess. The apparatus includes a compression biasing spring 32 pressing at one end against the back wall 24 and against the rear wall 30 of sample holder 34 at the other end. The holder 34 is mounted on a post-like member 35, which is guided through an aperture 37. A start switch 36 is mounted to the back wall offset from the member 35 so that when the sample holder 34 is pushed against the spring toward the back wall, the holder will depress the start switch to start operation of the instrument. Release of the sample holder will release the switch. The switch may also be mounted outside, say beneath the head 39, and operated upon movement of the head 39.

A surface coil 38 is mounted in the housing adjacent one of the permanent magnets 26 and 28. The coil produces the second field and acts as a source of energy for realignment and for sensing purposes. As seen in FIG. 1, the second field produced by the surface coil is transverse to the first or permanent magnet field. The surface coil has been selected for this embodiment because the depth of magnetization (i.e., extent of penetration of the field) is related to the diameter of the coil and can thus be controlled.

Figure 13:
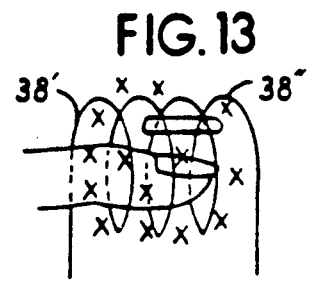
FIG. 13 is a schematic representation of the coil and magnet relationships which may be used in an arrangement of the type shown in FIG. 12.
Figure 14:
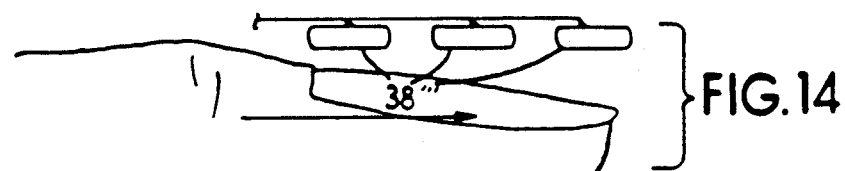
FIG. 14 is a schematic representation of a multicoil arrangement.
Figure 15:
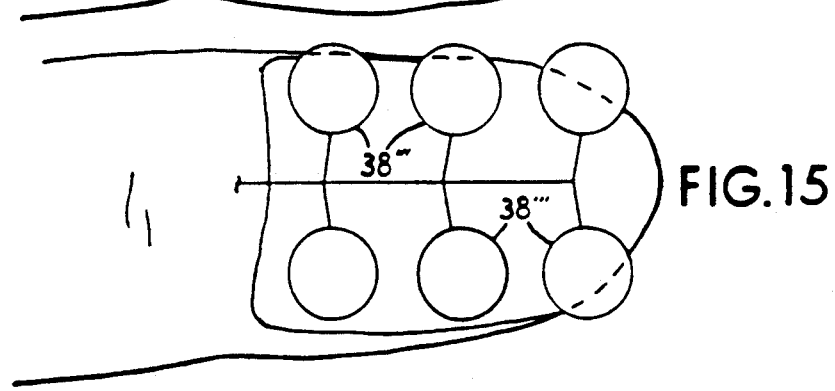
FIG. 15 is a top view of the elements of FIG. 14.

The surface coil 38 may be a single coil for both energization and sensing. The coil can also be an assembly in which there are multiple coils, each of which are for energization and sensing. Furthermore, the coil may be an assembly of at least two coils, where at least one is for energization and at least one other coil is for sensing. These alternatives are shown in FIGS. 13, 14 and 15.

The cover or housing 25A and 25B for the electronics is provided with an electronic interlock system (schematically shown as 56 in FIG. 3) so that unauthorized opening or removal of the cover will disable the electronics described hereinafter, thereby preventing unauthorized tampering or repair of the device which could destroy calibration and result in improper usage.

Physically the test is run by the patient inserting his finger into the instrument and pushing the sample holder toward the back wall 24 and into engagement with the start switch 36 to start the analysis as described hereinafter.

It will be noted that the finger is positioned so that the fingernail is located adjacent the surface coil. This positioning is chosen as the fingernail is dead tissue but has a bed of active blood vessels positioned just below the nail. These vessels are believed to provide an accurate testing site. In many other test sites, live body tissue or bone must be penetrated in order to test blood in a vessel, which means that the tissue or bone will emit signals due to testing which act as noise and may interfere with analysis of the blood for glucose concentration. The finger region is preferable, since the nail is essentially dead material and produces little, if any, interfering noise, thereby increasing the signal to noise ratio. It is believed that other body extremities can be tested, for example, the ear of either a human or other animals.

The testing circuit 40 includes a battery power supply 42. In a permanent installation, such as a doctor's office, hospital, etc., a commercial AC power supply and battery charger may be used to supply energy to the battery. Depression of the start switch activates the circuit and, thereby the microprocessor 44. The microprocessor activates an RF generator and cyclically-operated gate 46, which excites the surface coil 38 (or coil assembly) for applying the second field, raising the energy state and realigning the nuclei.

Figure 12:
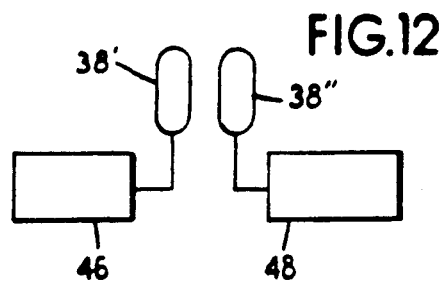
FIG. 12 is a schematic representation of an alternative circuit arrangement for use with separate energizing and receiving coils.

At the appropriate time and under control of the microprocessor, the RF generator is deactivated, thereby permitting the nuclei (dipoles) to relax or return to the first alignment. The surface coil then detects the energy released during relaxation and realignment. Those signals are received by receiver/gate 48, converted from analog signals to digital signals by the A/D converter 50 and fed to the microprocessor 44. A read only memory (ROM) 52 is provided for storing the program for use with the microprocessor in calibrating the machine and analyzing and displaying test results. If separate coils are used, then the circuit is changed so that the RF generator is connected to the energizing coil and the receiver is connected to the sensing coil as shown in FIG. 12.

The ROM is continuously energized by the battery 54. A cover interlock switch 56 is provided between the ROM 52 and battery 54 to deenergize the ROM in the event the electronics cover 25A or 25B is opened, removed or tampered with. In such an event, the switch 56 is opened and the program in the ROM is erased. In this instance, the ROM may be selected from the well-known classes of electrically erasable or alterable ROM's. The specific function of the ROM-cover interlock arrangement may be selected as desired, i.e., to generate an error message on the panel display, or simply to disable the apparatus from operating or exhibiting any panel display. Various other forms of electronic-type interlocks are well-known in the computer art.

The testing circuit 40 also includes a display 58, preferably digital, which is connected to the microprocessor and a group of status lamps (read 60, calibrate 62, display 64 and error 66), which indicate the status of the system's operation.

Figure 4A:
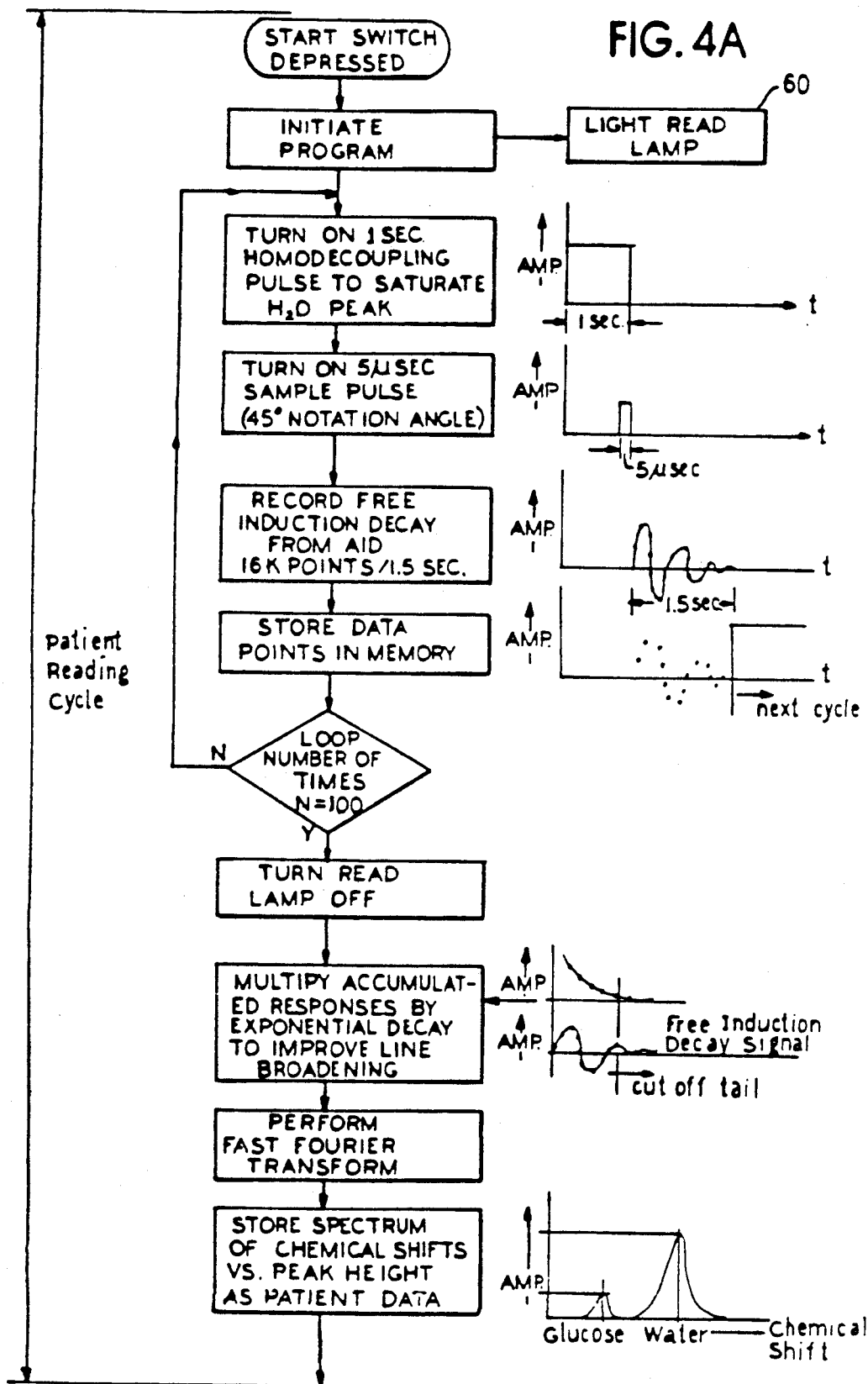
Figure 4B:
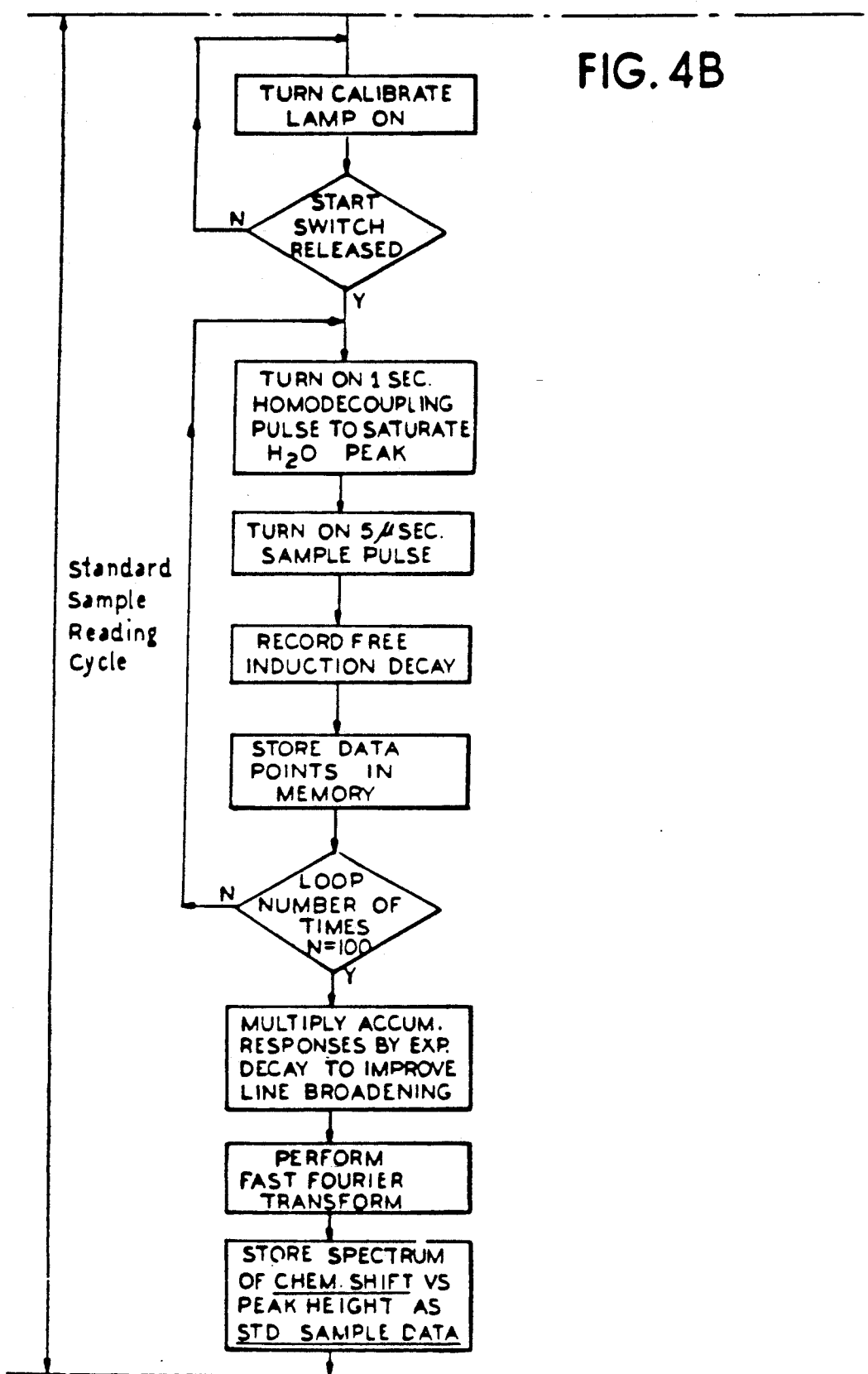

The ROM 52 includes a program as represented by the flow chart of FIGS. 4a–4c, whereby operation of the tester is controlled. In general, the operation of the tester is as follows:

1. A finger is inserted to depress the sample holder and activate the start switch.
2. The finger is tested.
3. The finger test results are stored in the RAM 45.
4. The finger is released and the standard sample moved to the test position.
5. The standard sample is tested.
6. The standard sample test results are stored in the RAM 45.
7. The standard sample test results are compared with predetermined calibration data previously entered in memory to determine if the standard sample data reading is still within preset and allowable tolerances.
8. Then the finger test results are compared with the sample standard test result data and the finger data is normalized and proportioned to determine glucose concentration.

Referring now to the flow diagram, FIGS. 4a through 4c, the various phases of the microprocessor and ROM are shown. These phases can considered as follows:

1. Patient reading cycle.
2. Standard sample reading cycle.
3. Operational system check.
4. Calculation of normalized patient data and standard sample for equal $H_2O$ peak.
5. Calculation of glucose level. Within each one of these broad steps are a series of smaller steps.

Referring first to FIG. 4a, the flow chart begins with depression of the starting switch 36, initiation of the program and activation of the read light 60. Next, a one second homodecoupling pulse (or a plurality of pulses) to saturate the water peak is activated. A five microsecond sample pulse is taken, and the free induction decay output from the A/D converter is noted. Next, the data points are stored in the memory 45 and the process is repeated (i.e., looped) perhaps one hundred times. In the right-hand column, there is shown a series of diagrams representing, the one second homodecoupling pulse, the five microsecond sampling pulse, the decay, and a Fourier transformation of the decay data points. The amplitude (Amp.) of the response is recorded along the Y-axis. After the samplings, the read lamp is deactivated, the accumulated responses are multiplied by an exponential decay to provide line broadening, a Fourier transformation is run, and a spectrum is stored as the chemical shifts versus the peak height as patient data.

Turning now to FIG. 4b, the standard sample reading cycle is next activated. Here the calibrate light is turned on, and the start switch is released. Once the switch is released one second homodecoupling pulse (or plurality of pulses) is provided, a five microsecond sampling pulse is taken, the free induction decay is recorded, and the data points are stored in the memory 45. The system is then repeated again, perhaps one hundred times. As in the patient reading cycle, the accumulated responses are multiplied by an exponential decay to improve line broadening, Fourier transforms are run and the spectrum of chemical shifts versus peak height is stored as sample data.

The standard sample initially contains predetermined amounts of the constituent material or materials being tested for and acts as a reference level. In order to assure that there has been no significant change in these value(s), the next step is an operational check where the spectrum of chemical shifts versus peak height data for the standard sample is recalled and compared to the standard data previously taken within allowable tolerances. If the error is not within an acceptable tolerance, the error display lamp 66 is lit and the operator notified. If the data is within an allowable error, the system proceeds to the next step. It is noted that on the right-hand side of FIG. 4c that a comparison is shown between the standard sample data and standard sample spectrum showing the allowable shifts, peak height and frequency with amplitude plotted along the Y-axis.

The next step is to normalize the patient data and standard sample data for equal water heights. Here the patient data is recalled and the standard sample data is recalled. Next, the patient data water peak height is scaled to match the standard sample data water peak height.

The system then executes the next step which is to calculate the glucose level. To do this a ratio is obtained of the patient data glucose peak height and the standard sample data peak height. This ratio is then multiplied by the known standard sample glucose to water ratio to obtain the patient reading and multiplied by a concentration factor (K) from the standard sample and expressed in milligrams per deciliter or some other convenient unit. Then the patient glucose level is displayed in relation to plasma level. Normal glucose concentration is ninety milligrams per deciliter.

This relationship is derived as follows:

1. The standard sample is prepared having a known glucose concentration expressed, for example, in milligram of glucose/deciliter of water (mg/dl) and is referred to as K.
2. A patient is tested and the water and glucose peak heights are obtained.
3. The standard sample is then tested for water and glucose peak heights.
4. The patient's water peak height is normalized by determining the ratio of water standard peak height/water patient peak height. This ratio can be referred to as gain.
5. The patient's glucose peak height is normalize d by multiplying the patient glucose peak height by the gain. The result is the normalized patient glucose $$\frac{\text{Glucose}}{\text{normalized}} = \frac{\text{(Water standard)}}{\text{(Water patient)}} \times \text{glucose patient}$$

6. In order to obtain the actual patient glucose concentration, expressed in units such as mg/dl, the normalized glucose now is divided by the glucose standard and the resulting ratio is multiplied by the concentration factor K. In other words:

$$\frac{\text{Patient glucose}}{\text{concentration}} = \frac{\text{Glucose normalized}}{\text{Glucose standard}} \times K$$

7. The entire expression which combines the steps of numbers 6-6 above can be stated as:

$$\frac{\text{Patient glucose}}{\text{concentration}} \left(\frac{mg}{dl}\right) =$$

$$K\left(\frac{mg}{dl}\right) \times \left(\frac{\text{Glucose patient peak height}}{\text{Glucose standard peak height}}\right) \times \left(\frac{\text{Water standard peak height}}{\text{Water patient peak height}}\right)$$

Figure 5A:
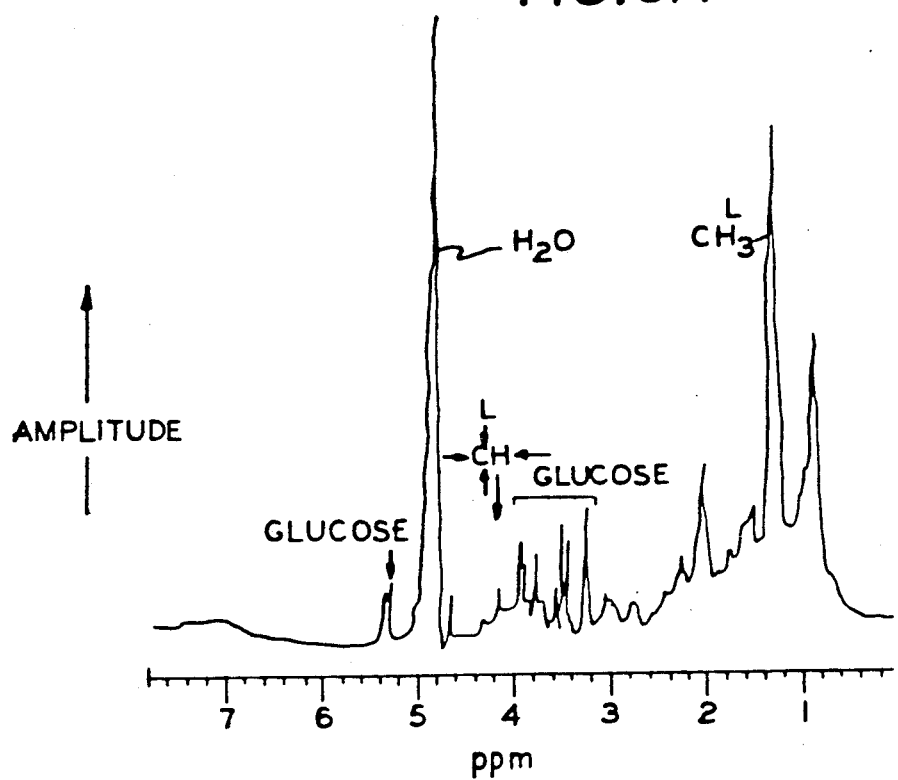
FIGS. 5a and 5b are representative NMR spectrums showing the water, glucose peaks and alcohol used for analysis.

In FIG. 5a, a $^1H$ typical blood spectrum is shown with the water ($H_2O$) and glucose peaks clearly shown. It is the ratio of the peak heights as determined from the calibration and test samples that permit determination of the test sample glucose concentration. FIG. 5a shows the work of Jay Block, "Analysis of Serum by High Yield NMR", Clin. Chem. 28/9, 1983, (1982) taken from normal blood serum. Sample volume is 0.4 ml serum to which has been added 0.1 ml of $^2H_2O$ for field lock. In addition, 10 mmol/1 of TSP was added to the $^2H_2O$ to serve as a reference to assign chemical shifts and peak area. The work was done on a WM 500 Burker spectrometer. Samples were maintained at 30° and a 1 second homodecoupling pulse was applied before the 5 millisecond sample pulse (45° notation angle) to saturate and reduce the $H_2O$ peak. A total of 16k data points was recorded in an acquisition on time of 1.5 seconds with 80 such transients averaged for each spectrum (2 min per spectrum). Even with the water peak suppressed, it is still the most prominent feature, however, the glucose peak which is four orders of magnitude lower is still easily identified. The glucose concentration is in the normal range of 90 mg/dl as measured by the conventional glucose oxidase procedure. Lactate was also detectable. It is also interesting to look at the glucose peak at 5.25 in the otherwise peak free region.

Figure 5B:
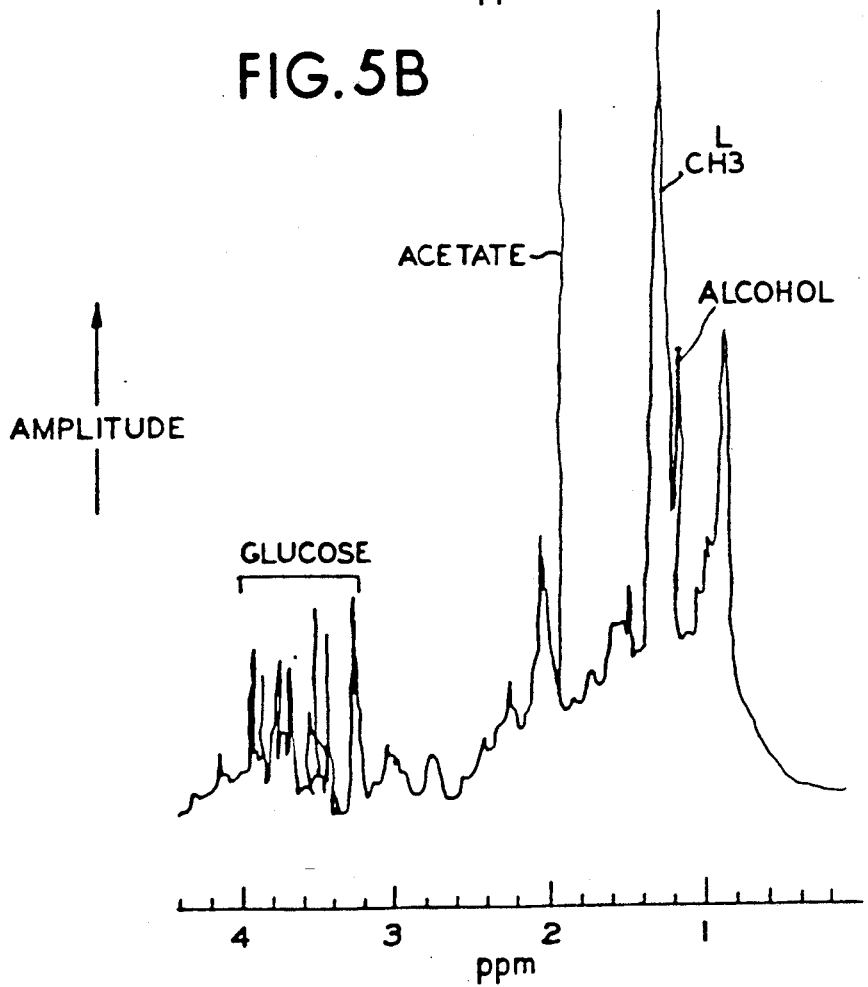

FIG. 5b is an enlarged portion of the $^1H$ blood spectrum of FIG. 5a showing the ethanol and water peaks, as also reported by Bock and showing the spectrum of serum obtained 30 minutes after ingestin 30 ml of vodka and water peaks, as also reported by Bock and is included to show a spectrum of serum obtained 30 minutes after ingesting 30 ml of vodka. The ethanol concentration measured by routine gaschromatographic method was only 30 mg/1, while the methyl resonance of ethanol at 1.20 ppm was detected with better than 40:1 signal to noise ratio. The methylene resonance is buried in the glucose region. In addition, a large peak appears at 1.93 ppm, the position of acetate, presumably derived from the oxidation of ingested ethanol. In serum from intoxicated patients, the ethanol resonance had a much greater intensity and dominated the spectra.

Figure 6:
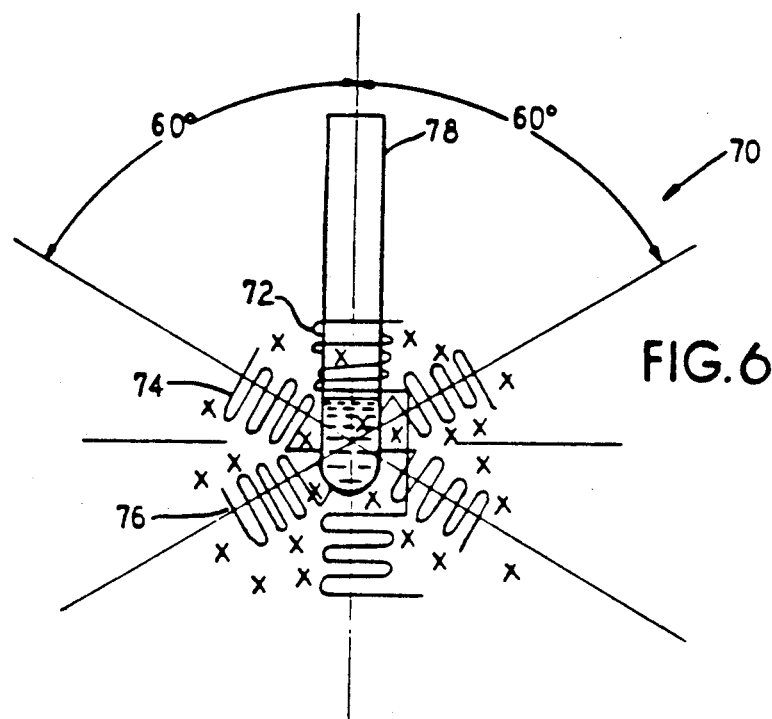
FIG. 6 is a schematic diagram showing a threecoil system for use in the instrument.
Figure 7:
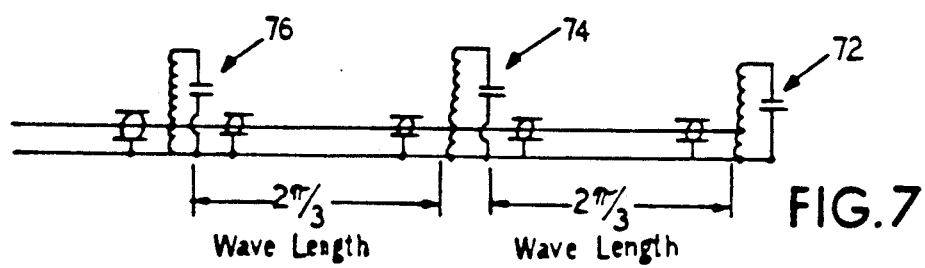
FIG. 7 is a schematic diagram showing the electrical connections for the three-coil system of FIG. 6.

Another embodiment 70 of this invention is shown in FIG. 6. In this embodiment, three coil pairs 72, 74 and 76, are provided which lie in the same plane and are equally spaced, that is at equally spaced 60° intervals. The coils are arranged to provide constructive interference at the center of the coils where a sample (such as a finger or test tube) is to be located. These coil pairs act as the energization or realignment coil and as the sensor, in a manner similar to the surface coil described hereinbefore. This arrangement is believed to provide better signal discrimination by increasing the signal-to-noise ratio. The coils are mounted in a housing similar to that shown in FIGS. 1 and 2 and are controlled by a circuit and in the manner similar to that described in connection with FIG. 3. Physically, the standard and sample is inserted into one of the coils, such as the test tube 78 into coil 72. The portion to be tested is located at the center of the coils as shown.

The test sample is then tested as described above with coils first acting as the energization or realignment magnets and then as sensors or receivers. In other regards, such as signal processing and concentration analysis, this system operates in the same manner as above.

Figure 8:
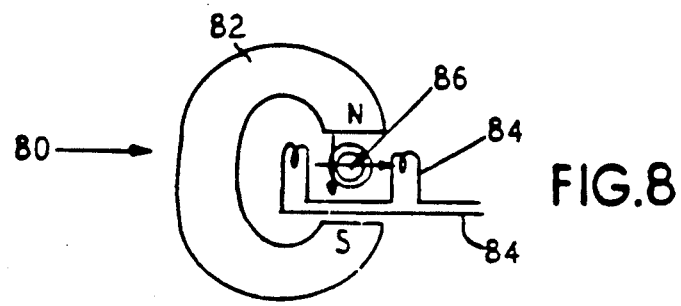
FIG. 8 shows an NMR probe for implantation in a body.
Figure 9:
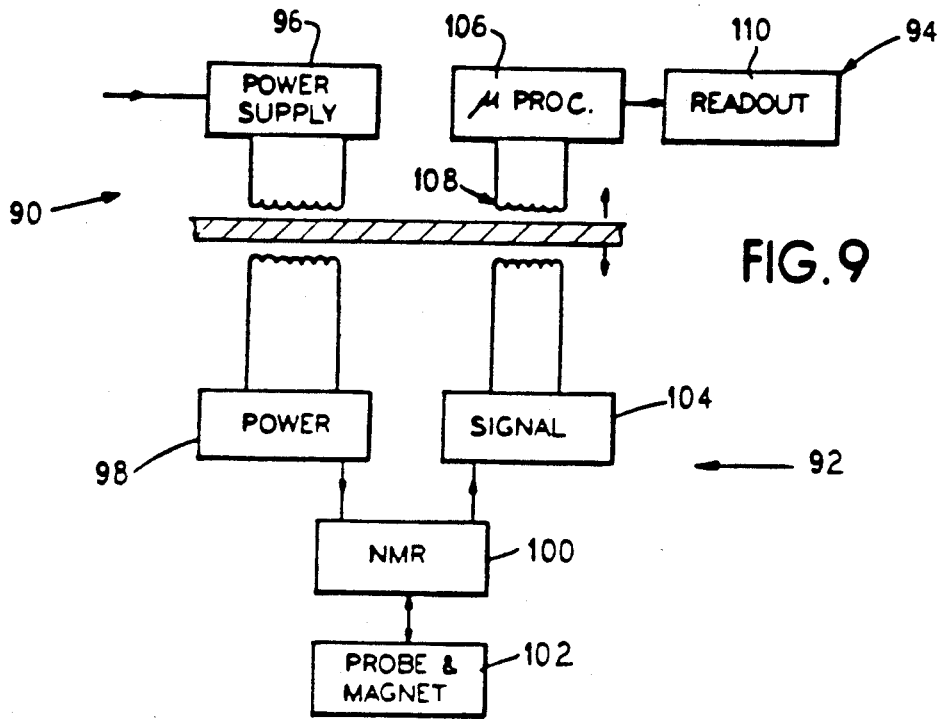
FIG. 9 is a schematic block-type diagram of the electrical circuit for use with the implantable probe of FIG. 8.

In those cases in which it may be desirable to implant a portion of the instrument, reference is made to FIGS. 8 and 9.

A third embodiment 80 is shown in FIG. 8, which is constructed to surround a blood vessel which is internal of or within a body, for example, a vein or artery in the body.

The test device includes the principal magnet 82, which in this case is C-shaped and a pair of RF coils 84. The vein or artery 86 is positioned between the coil pairs and the poles of the magnet. By so doing, blood in the vein or artery is subjected to the first magnetic field, and the energization or realignment field and relaxation is sensed by coils 84.

In a fourth embodiment, the test instrument 90 is constructed for surgical implantation as shown in FIG. 9. Such a device has two component parts: one part is the internal or implanted portion 92 and the other part is the external or power supply and sensing part 94. The two parts are electronically coupled by transformer-like members as described h(R)r(R)in.

In the fourth embodiment 90 an external AC power supply 96 is inductively coupled to an internal power supply 98. The internal power supply 98 powers the NMR unit 100, which is connected to probe and magnet unit 102. Signals from the probe and magnet are received by the receiver 104, which is inductively coupled to the microprocessor 106, through the coil element 108. The microprocessor then provides an output to the digital display 110 of the glucose concentration.

The magnet and probe assembly 102 is in the same form as that in FIG. 8 and is positioned to surround an artery. The signal processing is performed by the microprocessor in the same manner as with the other embodiments, particularly FIG. 3.

Figure 10:
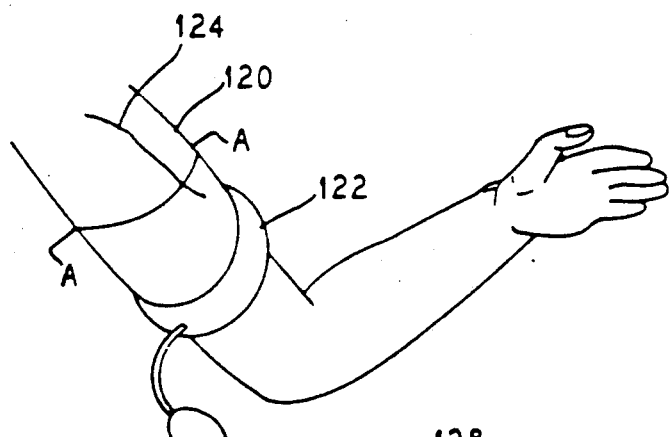
FIG. 10 shows a human arm having a distended vein for NMR testing.
Figure 11:
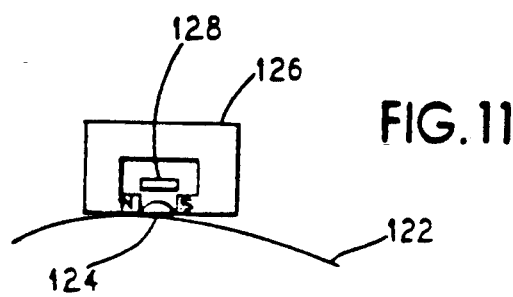
FIG. 11 is a fragmentary and sectional view of a magnetic probe for use in NMR analysis using a surface blood vessel.

In a fifth embodiment, a surface blood vessel, usually a vein, is distended and used to analyze for glucose concentration. Such an embodiment is shown in FIGS. 10 and 11, where a patient's arm 120 is shown surrounded by a pressurizable cuff 122 for causing a vein 124 to protrude or distend from the skin surface. In that situation, the NMR unit is fitted on either side of the protruding vessel at the surface of the arm. In this embodiment a C-shaped permanent magnet 126 is arranged so that its north and south poles (N & S) are on opposite sides of the vessel. A surface coil 128, like that in FIGS. 1–2, is employed for energization and realignment and sensing. Testing circuitry of the type shown in FIG. 3 is also employed in the embodiment of FIGS. 10 and II.

A principal advantage of the test instrument shown herein is that the device is smaller than the large NMR test instruments now used at hospitals, etc. The reason is that the present instruments include a large principal magnet for surrounding the body of a patient. Here, since the tested portion is a finger or other extremity, the principal magnet may be smaller so that the instrument may be mounted on a table top, carried in a brief case, or be even smaller. In order to achieve such a device, the magnet must be small in size, be of a comparatively light weight, such as one pound, and still exhibit an adequate field strength. Adequate strengths should be on the order of at least five to six kilogauss. One particularly suitable material containing Neodynium is manufactured by General Motors Corporation.

FIG. 12 shows the generator and gate 46 and the receiver 46 and gate 48, respectively, connected to separate transmit and receive coils 38', 38".

FIG. 13 shows an embodiment of the coils 38' and 38" along with the field directions, including the bias field Ho, at 90° with respect to one another.

FIGS. 14 and 15 illustrate the use of a plurality of surface coils 38", which are connected for additive fields, as a single transmit/receive arrangement.

Figure 16:
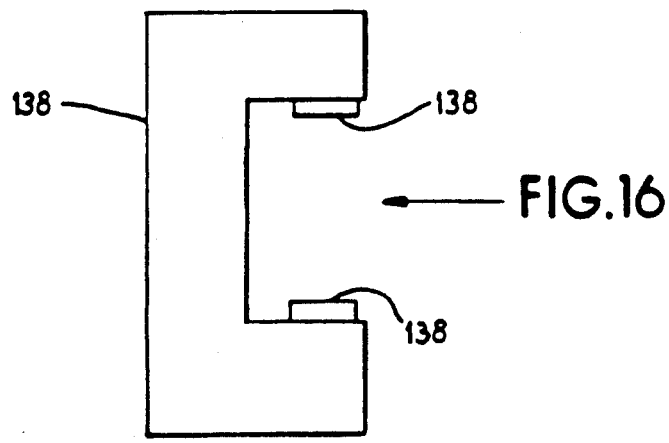
FIG. 16 is a side view of an alternative C-shaped magnet which may replace the magnetic structure of FIGS. 1 and 2.

FIG. 16 shows an alternate bias magnet, similar to that shown in FIG. 11 The magnet 138 comprises a pair of spaced pole pieces 132, 134, which define a gap for receiving, in this example, a finger.

Although the invention has been described with respect to preferred embodiments, it is not to be so limited, as changes and modifications can be made which are within the full intended scope of the invention as defined by the appended claims.

We claim:

1. In a nuclear magnetic resonance spectroscopy apparatus for testing fluids for the presence of constituents, said apparatus being of the type in which a first magnetic field aligns $^1H$ protons to an initial position, and in which a second magnetic field is cyclicly energized and deenergized to cause alignment of the $^1H$ protons to a second position and realignment to said initial position, and in which the magnetic changes resulting during realignment are detected and analyzed, the improvement comprising:

first magnet means comprising a pair of permanent bar magnets each including a north pole and a south pole, second magnet means for creating said second magnetic field, said second magnet means comprising a plurality of additively connected surface coils for both transmitting energization and sensing;

mounting means for mounting said first magnet means, said mounting means comprising a pair of spaced apart members for positioning said pair of bar magnets space apart with the north pole of each said bar magnet secured to one of said members and the south pole of each said bar magnet secured to the other of said members, said first magnet means, said second magnet means and said mounting means providing a cavity defining a test region therein for receiving a sample of the fluid to be tested, said first magnetic field being substantially uniform in field strength and direction throughout said test region;

said second magnet means being operatively disposed with respect to said test region for being magnetically coupled to the fluid sample to be tested;

first and second members connecting said pair of spaced apart members, said first connecting member including an aperture therethrough for access of said fluid sample into said test region;

circuit means for detecting and analyzing said magnetic changes;

said second connecting member having switch means operatively associated therewith for initiating operation of said circuit means;

a sample holder containing a standard sample of known concentrations of the constituents to be investigated;

said standard sample holder being initially disposed in said test region; and means for biasing said sample holder to urge said sample holder toward said second connecting member and to initially locate said standard sample in said test region and capable of being operatively coupled to said second magnet means when said second magnet means is energized;

said switch means being activated in response to the movement of said standard sample holder out of said test region to contact and operate said switch means when said fluid sample to be tested is moved into said test region.

* * * * *